United States Patent
Bebbington et al.

(10) Patent No.: US 8,834,870 B2
(45) Date of Patent: Sep. 16, 2014

(54) TREATMENT OF LEUKEMIAS AND CHRONIC MYELOPROLIFERATIVE DISEASES WITH ANTIBODIES TO EPHA3

(75) Inventors: Christopher R. Bebbington, South San Francisco, CA (US); Geoffrey T. Yarranton, South San Francisco, CA (US); Varghese Palath, South San Francisco, CA (US)

(73) Assignee: Kalobios Pharmaceuticals, Inc., South San Francisco, CA (US)

( * ) Notice: Subject to any disclaimer, the term of this patent is extended or adjusted under 35 U.S.C. 154(b) by 625 days.

(21) Appl. No.: 12/718,768

(22) Filed: Mar. 5, 2010

(65) Prior Publication Data

US 2010/0226930 A1 Sep. 9, 2010

Related U.S. Application Data

(60) Provisional application No. 61/168,130, filed on Apr. 9, 2009, provisional application No. 61/158,285, filed on Mar. 6, 2009.

(51) Int. Cl.
*A61K 39/395* (2006.01)

(52) U.S. Cl.
USPC .................................... 424/130.1; 530/387.1

(58) Field of Classification Search
None
See application file for complete search history.

(56) References Cited

FOREIGN PATENT DOCUMENTS

| WO | WO 2004/069264 A1 | | 8/2004 |
|---|---|---|---|
| WO | WO/2008/112192 | * | 9/2008 |
| WO | WO 2008/112192 A2 | | 9/2008 |

OTHER PUBLICATIONS

Cilloni et al. Blood, vol. 112, No. 11 Nov. 2008.*
Surawska et al. (Cytokine & Growth Factor Reviews, vol. 15, pp. 419-433, 2004).*
Arruga, et al., "EphA3 is abnormally expressed in chronic myeloplipherative disorders and could represent a new molecular target," *Proceedings of the American Association for Cancer Research Annual Meeting*, vol. 50, p. 692 (Apr. 2009).
Cilloni, et al., "EphA3 is Abnormally Expressed in Chronic Myeloproliperative Disorders and Can be Targeted by Dasatinib or by Monoclonal Antibodies," *Haematologica*, vol. 92 Supplement 2 (248), Abstract 0665, 2 pages (2007).
Cilloni, et al., "EphA3 Kinase Is Constitutively Activated in Chronic Myeloid Leukaemia During Progression to Accelerated and Blast Crisis and it Could Represent a New Molecular Target," *Blood* vol. 112(11), p. 399, Abstract 1092 (Nov. 2008).
Lackmann, et al. "Expression and function in modulating tumor cell-cell contacts identifies EphA3 as candidate cell-surface receptor for tumor targeting strategies," *Proceedings of the Annual Meeting of the American Association for Cancer Research, American Cancer Association for Cancer Research*, vol. 45, p. 1015, #4406 (Mar. 27, 2004).
Palath, et al., "A Recombinant Human Antibody to EphA3 with Pro-Apoptotic and Enhanced ADCC Activity Shows Selective Cytotoxicity against Myeloid Leukemia Cells and CD123-Positive Leukemic Stem Cells," *Blood*, vol. 114(22), p. 688, Abstract 1728 (Nov. 2009).
Vearing, et al., "Concurrent Binding of Anti-EphA3 Antibody and Ephrin-A5 Amplifies EphA3 Signaling and Downstream Responses: Potential as EphA3-Specific Tumor-Targeting Reagents," *Cancer Research*, vol. 65(15), pp. 6745-6754 (Aug. 1, 2005).
Zhou, et al., "Development of a Simple and Rapid Method for Producing Non-Fucosylated Oligomannose Containing Antibodies with Increased Effector Fuction," *Biotechnology and Bioengineering*, vol. 99(3), pp. 652-665 (Feb. 15, 2008).
International Search Report and Written Opinion for PCT/US2010/026413, dated Aug. 13, 2010, 20 pages.
Bohme et al., "PCR mediated detection of a new human receptor-tyrosine-kinase, HEK 2", *Oncogne*, 1993, vol. 8, pp. 2857-2862.
Dottori et al.,"Cloning and Characterization of EphA3 (HEK) Gene Promoter: DNA Mehthylation Regulates Expression in Hematopoietic Tumor Cells" *Blood*, 1999, vol. 94, No. 7, pp. 2477-2486.
Wicks et al., "Molecular cloning of HEK, the gene encoding a receptor tyrosine kinase expressed by human lymphoid tumor cell liens", *Proc. Natl. Acad. Sci. USA*, 1992, vol. 89, pp. 1611-1615.

* cited by examiner

*Primary Examiner* — Laura B Goddard
*Assistant Examiner* — Meera Natarajan
(74) *Attorney, Agent, or Firm* — Kilpatrick Townsend & Stockton LLP

(57) ABSTRACT

The invention provides methods and compositions comprising anti-EphA3 antibodies for the treatment of myeloproliferative disorders.

30 Claims, 4 Drawing Sheets

TREATMENT OF LEUKEMIAS AND CHRONIC MYELOPROLIFERATIVE DISEASES WITH ANTIBODIES TO EPHA3

CROSS-REFERENCE TO RELATED APPLICATIONS

This application claims benefit of U.S. provisional application No. 61/158,285, filed Mar. 6, 2009 and U.S. provisional application No. 61/168,130 filed Apr. 9, 2009. Each application is herein incorporated by reference.

BACKGROUND OF THE INVENTION

Eph receptor tyrosine kinases (Ephs) belong to a large group of receptor tyrosine kinases (RTKs), kinases that phosphorylate proteins on tyrosine residues. Ephs and their membrane bound ephrin ligands (ephrins) control cell positioning and tissue organization (Poliakov, et al., *Dev Cell* 7:465-80, 2004). In contrast to other receptor tyrosine kinases, Eph receptor activation does not only require ligand binding and dimerization but also involves preformed ligand oligomers. Thus, tyrosine phosphorylation of Eph receptors requires presentation of ephrin ligands in their clustered or membrane-attached forms (Davis et al., *Science* 266:816-819, 1994). Functional and biochemical Eph responses occur at higher ligand oligomerization states (Stein et al., *Genes Dev* 12:667-678, 1998).

Among other patterning functions, various Ephs and ephrins have been shown to play a role in vascular development. The de-regulated re-emergence of some ephrins and their receptors in adults also has been observed to contribute to tumor invasion, metastasis and neo-angiogenesis. For example, dominant-negative, soluble EphA2 or A3 proteins exhibit effects on ephrin-induced endothelial cell function in vitro, and tumor angiogenesis and progression in vivo (Nakamoto, et al., *Microsc Res Tech* 59:58-67, 2002; Brantley-Sieders, et al., *Curr Pharm Des* 10:3431-42, 2004; Brantley, et al. *Oncogene* 21:7011-26, 2002; Cheng, et al. *Neoplasia* 5:445-56, 2003; and Dobrzanski, et al. *Cancer Res* 64:910-9, 2004). Furthermore, Eph family members have been found to be over-expressed on tumor cells from a wide variety of human solid tumors (Brantley-Sieders, et al., *Curr Pharm Des* 10:3431-42, 2004; Marme, *Ann Hematol* 81 Suppl 2:S66, 2002; and Booth, et al., *Nat Med* 8:1360-1, 2002).

Epha3 has also been reported to be activated and overexpressed on CD34$^+$ cells in chronic myeloid leukemia (CML) patients in the accelerated phase and blast crisis stage (Cilloni et al., American Society of Hematology, Abstract 1092, 2008 (available online Nov. 14, 2008)). Cilloni et al. reported that when primary CML cells or EphA3-transfected normal cells were incubated with a specific monoclonal antibody that they referred to as a blocking antibody, the antibody induced a significant reduction of proliferation in primary cells and transfected cells, reduced colony growth and induced changes to the adhesion properties. The antibody did not induce any significant changes in normal control cells or cells from CML patient in the chronic stage.

There have been no reports that EphA3 is a therapeutic target in other myeloproliferative disorder.

BRIEF SUMMARY OF THE INVENTION

The invention is based, in part, on the discovery that neoplastic myeloid cells, including neoplastic myeloid stem cells, in the bone marrow and peripheral blood samples obtained from a patient that has chronic myeloid leukemia (CML), acute myeloid leukemia (AML), chronic myelomonocytic leukemia (CMML), juvenile myelomonocytic leukemia (JMML), myelodysplastic syndrome (MDS), polycythemia vera (PV), essential thrombocythemia (ET), or idiopathic myelofibrosis (IM), express EphA3 protein on the cell surface and that such cells can be killed using an activating anti-EphA3 antibody or an antibody that induces ADCC.

In one aspect, the invention provides a method of killing AML cells, MDS cells, CMML cells, JMML cells, CML cells, PV cells, ET cells, or IM cells, the method comprising contacting the cells with an anti-EphA3 antibody. In one aspect, the invention provides a method of treating a patient that has AML, CCML, JMML, MDS, CML, PV, ET or IM, the method comprising administering an anti-EphA antibody to the patient. In some embodiments, the anti-EphA3 antibody dimerizes EphA3. In some embodiments, the anti-EphA3 antibody activates EphA3 and kills the target cells by apoptosis. In some embodiments, the anti-EphA3 antibody kills the target cells by inducing antibody-dependent cell-mediated cytotoxicity (ADCC). In some embodiments, the invention provides a method of killing myeloproliferative disorder cells that express EphA3 on the surface, the method comprising contacting the cells with an anti-EphA3 antibody, wherein the anti-EphA3 antibody (i) activates EphA3 and (ii) induces antibody-dependent cell-mediated cytotoxicity (ADCC). In some embodiments, the invention provides a method of treating a patient that has a myeloproliferative disorder and has myeloproliferative disorder cells the express EphA3 on the cell surface, the method comprising administering a therapeutically effective amount of an anti-EphA3 antibody to the patient, wherein the anti-EphA3 antibody (i) activates EphA3 and (ii) induces ADCC. In some embodiments, the invention provides a method of killing myeloproliferative disorder cells that express EphA3 on the surface, the method comprising contacting the cells with an anti-EphA3 antibody that activates EphA3 or induces ADCC, wherein the myeloproliferative disorder cells are acute myeloid leukemia (AML) cells or myelodysplastic syndrome (MDS) cells. In some embodiments, the invention provides a method of treating a patient that has a myeloproliferative disorder and has myeloproliferative disorder cells the express EphA3 on the cell surface, the method comprising administering a therapeutically effective amount of an anti-EphA3 antibody to the patient, wherein the anti-EphA3 antibody activates EphA3 or induces ADCC, wherein the myeloproliferative disorder is AML or MDS.

In some embodiments, the anti-EphA3 antibody for use in the methods of the invention is a recombinant or chimeric antibody. In some embodiments, the anti-EphA3 antibody is a human antibody. The anti-EphA3 antibody may be a polyclonal antibody or a monoclonal antibody. In some embodiments, the anti-EphA3 antibody is a multivalent antibody that comprises a Fab, a Fab', or an Fv. In some embodiments, the antibody is a F(ab')$_2$. In some embodiments, the anti-EphA3 antibody competes for EphA3 binding with mAb IIIA4. In some embodiments, the antibody binds to the same epitope as mAB IIIA4. In typical embodiments, the antibody does not block ephrin ligand binding, e.g., ephrinA5 binding, to EphA3. In some embodiments the anti-EphA3 antibody comprises the V$_H$ and V$_L$ regions of mAb IIIA4. In some, embodiments, the anti EphA3 antibody comprises the V$_H$ and V$_L$ region CDR1, CDR2 and CDR3 of mAb IIIA4. In some embodiments, the antibody comprises the V$_H$ region CDR3 and V$_L$ region CDR3 of mAb IIIA4. In some embodiments, the antibody induces ADCC. Thus, in some embodiments the antibody has an active isotype, e.g., the antibody has a human heavy chain constant region that is a gamma-1 or gamma-3 region. In some embodiments, the antibody does not induce ADCC, e.g., the antibody has a human heavy chain constant region that is a gamma-2 or gamma-4 region.

In the context of this invention, "an anti-EphA3 antibody that activates EphA3 or induces ADCC" refers to an antibody that (i) activates EphA3 (ii) induces ADCC, or (iii) activates and induces ADCC.

In some embodiments of the invention, a myeloproliferative disorder patient is treated with an anti-EphA3 antibody as described herein and also receives treatment with another therapeutic agent for the disease. Thus, in some embodiments, the method comprises administering one or more additional therapeutic agents. For example, when the myeloproliferative disorder is CML, additional therapeutic agents include imatinib mesylate, nilotinib, dasatinib, or another chemotherapeutic agent. When the myeloproliferative disorder is AML, the additional therapeutic agents may be cytosine arabinoside alone or in combination with daunorubicin.

Normal myeloid blast cells and stem cells do not express EphA3 on the cell surface. Thus, in additional aspects, the invention provides a method of identifying a patient having a myeloproliferative disorder that is a candidate for treatment with an anti-EphA3 antibody, wherein the method comprises detecting EphA3 expression by myeloid blast cells and/or stem cells from the patient.

In some embodiments, the invention provides a method of determining that an AML patient or MDS patient is a candidate for treatment with an anti-EphA3 antibody, the method comprising: providing a sample from the patient, where the sample comprises myeloproliferative disorder cells; and detecting expression of EphA3 on the myeloproliferative disorder cells. In some embodiments, the invention provides a method of determining that a CMPD patient is a candidate for treatment with an anti-EphA3 antibody, the method comprising: providing a sample comprising neoplastic stem cells from the patient; and detecting expression of EphA3 by the neoplastic stem cells. In some embodiments, the invention provides a method of monitoring the efficacy of treatment of a patient having a myeloproliferative disorder with EphA3+ myeloproliferative cells, wherein the myeloproliferative disorder is AML or MDS, the method comprising: obtaining a sample comprising myeloproliferative disorder stem cells and/or blast cells from the patient following a therapeutic treatment for the myeloproliferative disorder; and detecting expression of EphA3 on the myeloproliferative disorder stem cells and/or blast cells. Ins some embodiments, the invention provides a method of monitoring the efficacy of treatment of a CMPD patient that has neoplastic myeloproliferative disorder stem cells that express EphA3, the method comprising: obtaining a sample comprising the neoplastic stem cells from the patient following a therapeutic treatment for the CMPD; and detecting expression of EphA3 on the stem cells.

EphA3 expression can be detected using commonly known techniques. Thus, in some embodiments detecting expression of EphA3 comprises detecting protein expression on the cell surface, e.g., using flow cytometry. In some embodiments, the step of detecting expression of EphA3 comprises detecting EphA3 RNA levels, e.g., using an amplification reaction such as RT-PCR.

The invention further provides a pharmaceutical composition comprising an anti-EphA3 antibody as described herein for use in treating a patient that has a myeloproliferative disorder.

DETAILED DESCRIPTION OF THE INVENTION

Definitions

Figure 1:
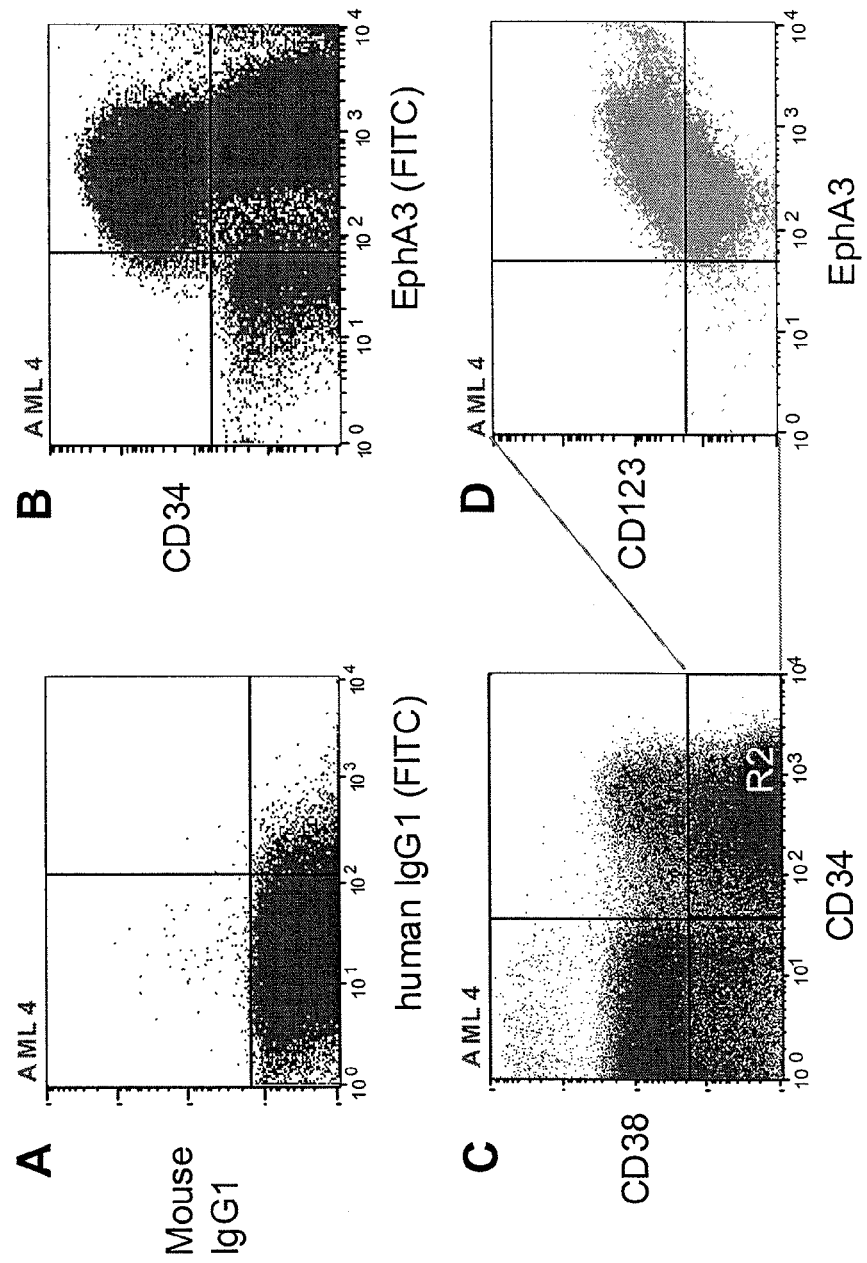
FIG. 1 provides data showing binding of an engineered human anti-EphA3 antibody to leukemic stem cells. AML primary bone marrow cells were stained with: engineered human anti-EphA3 antibody or IgG1 control and FITC-conjugated anti-human IgG; PE-conjugated anti-CD34; PEcy5-conjugated anti-CD38; and APC-conjugated anti-CD123 antibodies for flow cytometry analysis (50,000 events per sample). A) isotype control gating for CD34 analysis. (B) Sample stained with anti-EphA3 and anti-CD34. (C) Sample stained for CD34 and CD38 (R2 represents CD34+CD38− cells). (D) Identification of EphA3 and CD123 expression on CD34+CD38− cells (R2 gate).

The term "myeloproliferative disorders" as used herein refers to certain chronic myeloproliferative diseases classified as chronic myeloid proliferative disorders (CMPDs); acute myeloid leukemia (AML); myeloid dysplastic syndrome (MDS); chronic myelomonocytic leukemia (CMML); and juvenile myelomonocytic leukemia (JMML). In the context of this invention, a "myeloproliferative disorder" thus refers to chronic myeloid leukemia (CML); polycythemia vera (PV); essential thrombocythemia (ET); idiopathic myelofibrosis (IM), which is also referred to as primary myelofibrosis; AML; MDS; CMML; and JMML, The term "JMML" encompasses all diagnoses referred to as Juvenile Chronic Myeloid Leukemia (JCML), Chronic Myelomonocytic Leukemia of Infancy, and Infantile Monosomy 7 Syndrome. Myeloproliferative disorders can be diagnosed using known criteria, e.g., the World Health Organization (WHO) criteria, the French-American-British (FAB) classification system, the International Prognostic Scoring System (IPSS), and the like. In the 2008 WHO classification, CMPDs are referred to as myeloproliferative neoplasms (MPNs). Myeloproliferative disorders are often characterized by the presence of particular mutations. For example, CML is characterized by the presence of BCR-ABL. PV, ET, and IM are "non-BCR- ABL" (also referred to herein as "BCR-ABL minus" or "BCR-ABL negative") CMPDs, as these disorders do not have BCR-ABL. However, BCR-ABL negative disorders are often characterized by the presence of JAK2 mutations, which are rare in CML.

The term "myeloid stem cells" or "stem cells" as used herein are hematopoietic stem cells that are characterized as CD34+, CD123+, and CD38−.

The term "myeloproliferative disorder cells" refers to neoplastic myeloid cells that are characteristic of a myeloproliferative disorder. The term encompasses myeloid cells that may not yet be considered to be malignant, e.g., such as the myeloid cells that are characteristic of myelodysplastic syndrome, as well as malignant cells, such as malignant acute leukemia cells. The term encompasses both blast cells and stem cells.

The terms "cancer cell" or "tumor cell" are used interchangeably to refer to a neoplastic cell. The term includes cells that are benign as well as malignant. Neoplastic transformation is associated with phenotypic changes of the tumor cell relative to the cell type from which it is derived. The changes can include loss of contact inhibition, morphological changes, and aberrant growth. (see, Freshney, *Culture of Animal Cells a Manual of Basic Technique* (3$^{rd}$ edition, 1994).

"Inhibiting growth of a cancer" in the context of the invention refers to slowing growth and/or reducing the cancer cell burden of a patient that has a myeloproliferative disorder. "Inhibiting growth of a cancer" thus includes killing cancer cells.

As used herein "EphA3" refers to the Eph receptor A3. This receptor has also been referred to as "Human embryo kinase", "hek", "eph-like tyrosine kinase 1", "etk1" or "tyro4". EphA3 belongs to the ephrin receptor subfamily of the protein-tyrosine kinase family. EPH and EPH-related receptors have been implicated in mediating developmental events. Receptors in the EPH subfamily typically have a single kinase domain and an extracellular region containing a Cys-rich domain and 2 fibronectin type III repeats. The ephrin receptors are divided into 2 groups based on the similarity of their extracellular domain sequences and their affinities for binding ephrin-A and ephrin-B ligands. EphA3 binds ephrin-A ligands. EphA3 nucleic acid and protein sequences are known. An exemplary human EphA3 amino acid sequence is available under accession number (EAW68857).

For the purposes of the present invention, "activation" of EphA3 causes phosphorylation of EphA3 and apoptosis. An antibody that activates EphA3 or "an activating antibody" causes phosphorylation of EphA3 and apoptosis and is therefore considered to be an agonist in the context of this invention. EphA3 can be activated by dimerization, which leads to apoptosis. In some embodiments, an antibody that activates EphA3 competes with mAb IIIA4 for binding to EphA3. Typically, an "activating" antibody binds to the ligand binding domain (amino acids 29-202 of EphA3) wherein amino acid residues 131, 132, and 136 are important for binding. In some embodiments, the activating antibody binds to a site encompassing the residues 131, 132, and 136 within the ligand binding domain of human EphA3 protein.

In the present invention, "EphA3 antibody" or "anti-EphA3 antibody" are used interchangeably to refer to an antibody that specifically binds to EphA3. In some embodiments, the antibody can dimerize EphA3. The term encompasses antibodies that bind to EphA3 in the presence of ephrin ligand (e.g., ephrin-A5) binding, as well as antibodies that bind to the ligand binding site.

An "EphA3 antibody that binds to EphA3 in the presence of binding of an ephrin ligand" refers to an antibody that does not significantly prevent binding of an ephrin ligand, such as ephrin-A5, to EphA3. The presence of such an antibody in a binding reaction comprising EphA3 and an ephrin ligand, e.g., ephrin-A5, reduces ephrin ligand binding to EphA3 by less than about 30%, typically less than 20% or 10%.

The term "mAb IIIA4" refers to monoclonal antibody IIIA4 that was originally raised against LK63 human acute pre-B leukemia cells to affinity isolate EphA3 (Boyd, et al. *J Biol Chem* 267:3262-3267, 1992). mAb IIIA4 binds to the native EphA3 globular ephrin-binding domain (e.g., Smith, et al., *J. Biol. Chem* 279:9522-9531, 2004). It is deposited in the European Collection of Animal Cell Cultures under accession no. 91061920 (see, e.g., EP patent no. EP0590030).

An "antibody having an active isotype" as used herein refers to an antibody that has a human Fc region that binds to an Fc receptor present on immune effector cells. "Active isotypes" include IgG1, IgG3, IgM, IgA, and IgE. The term encompasses antibodies that have a human Fc region that comprises modifications, such as mutations or changes to the sugar composition and/or level of glycosylation, that modulate Fc effector function.

An "Fc region" refers to the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ. It is understood in the art that the boundaries of the Fc region may vary, however, the human IgG heavy chain Fc region is usually defined to comprise residues C226 or P230 to its carboxyl-terminus, using the numbering is according to the EU index as in Kabat et al. (1991, NIH Publication 91-3242, National Technical Information Service, Springfield, Va.). The term "Fc region" may refer to this region in isolation or this region in the context of an antibody or antibody fragment. "Fc region" includes naturally occurring allelic variants of the Fc region as well as modifications that modulate effector function. Fc regions also include variants that don't result in alterations to biological function. For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, et al., *Science* 247:306-1310, 1990).

As used herein, an "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "antibody" as used herein includes antibody fragments that retain binding specificity. For example, there are a number of well characterized antibody fragments. Thus, for example, pepsin digests an antibody C-terminal to the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies.

Antibodies include $V_H$-$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ which may be expressed from a nucleic acid including $V_H$- and $V_L$-encoding sequences either joined directly or joined by a peptide-encoding linker (e.g., Huston, et al. *Proc. Nat. Acad. Sci. USA*, 85:5879-5883, 1988). While the $V_H$ and $V_L$ are connected to each as a single polypeptide chain, the $V_H$ and $V_L$ domains associate non-covalently. Alternatively, the antibody can be another fragment. Other fragments can also be generated, e.g., using recombinant techniques, as soluble proteins or as fragments obtained from display methods. Antibodies can also include diantibodies and miniantibodies. Antibodies of the invention also include heavy chain dimers, such as antibodies from camelids. For the purposes of this inventor, antibodies are employed in a form that can activate EphA3 present on the surface of myeloproliferative cells or that can kill myeloproliferative cells by ADCC. Thus, in some embodiments an antibody is dimeric. In other embodiments, the antibody may be in a monomeric form that has an active isotype. In some embodiments the antibody is in a multivalent form, e.g., a trivalent or tetravalent form, that can cross-link EphA3.

As used herein, "V-region" refers to an antibody variable region domain comprising the segments of Framework 1, CDR1, Framework 2, CDR2, and Framework3, including CDR3 and Framework 4, which segments are added to the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol* 1997, 273(4)). Definitions of antigen combining sites are also described in the following: Ruiz et al., IMGT, the international ImMunoGeneTics database. *Nucleic Acids Res.*, 28, 219-221 (2000); and Lefranc, M.-P. IMGT, the international ImMunoGeneTics database. *Nucleic Acids Res.* January 1; 29(1):207-9 (2001); MacCallum et al, Antibody-antigen interactions: Contact analysis and binding site topography, *J. Mol. Biol.*, 262 (5), 732-745 (1996); and Martin et al, *Proc. Natl Acad. Sci. USA,* 86, 9268-9272 (1989); Martin, et al, *Methods Enzymol.,* 203, 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

As used herein, "humanized antibody" refers to an immunoglobulin molecule in CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., *Nature* 321:522-525; 1986; Riechmann et al., *Nature* 332:323-327, 1988; Verhoeyen et al., *Science* 239:1534-1536, 1988); Presta, *Curr. Op. Struct. Biol.* 2:593-596, 1992; U.S. Pat. No. 4,816,567), including techniques such as "superhumanizing" antibodies (Tan et al., *J. Immunol.* 169: 1119, 2002) and "resurfacing" (e.g., Staelens et al., *Mol. Immunol.* 43: 1243, 2006; and Roguska et al., *Proc. Natl. Acad. Sci USA* 91: 969, 1994).

A "HUMANEERED™" antibody in the context of this invention refers to an engineered human antibody having a binding specificity of a reference antibody. An engineered human antibody for use in this invention has an immunoglobulin molecule that contains minimal sequence derived from a donor immunoglobulin. In some embodiments, the engineered human antibody may retain only the minimal essential binding specificity determinant from the CDR3 regions of a reference antibody. Typically, an engineered human antibody is engineered by joining a DNA sequence encoding a binding specificity determinant (BSD) from the CDR3 region of the heavy chain of the reference antibody to human $V_H$ segment sequence and a light chain CDR3 BSD from the reference antibody to a human $V_L$ segment sequence. A "BSD" refers to a CDR3-FR4 region, or a portion of this region that mediates binding specificity. A binding specificity determinant therefore can be a CDR3-FR4, a CDR3, a minimal essential binding specificity determinant of a CDR3 (which refers to any region smaller than the CDR3 that confers binding specificity when present in the V region of an antibody), the D segment (with regard to a heavy chain region), or other regions of CDR3-FR4 that confer the binding specificity of a reference antibody. Methods for engineering human antibodies are provided in US patent application publication no. 20050255552 and US patent application publication no. 20060134098.

The term "human antibody" as used herein refers to an antibody that is substantially human, i.e., has FR regions, and often CDR regions, from a human immune system. Accordingly, the term includes humanized and HUMANEERED™ antibodies as well as antibodies isolated from mice reconstituted with a human immune system and antibodies isolated from display libraries.

A "hypofucosylated" antibody preparation refers to an antibody preparation in which the average content of α1,6-fucose is less than 50% of that found in naturally occurring IgG antibody preparations. As understood in the art, "hypofucosylated" is used in reference to a population of antibodies.

An "afucosylated" antibody lacks α1,6-fucose attached to the CH2 domain of the IgG heavy chain.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a heterologous protein will often refer to two or more subsequences that are not found in the same relationship to each other in nature.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The phrase "specifically (or selectively) binds" to an antibody or "specifically (or selectively) immunoreactive with," when referring to a protein or peptide, refers to a binding reaction where the antibody binds to the protein of interest. In the context of this invention, the antibody typically binds to EphA3 with an affinity that is at least 100-fold better than its affinity for other antigens.

The term "equilibrium dissociation constant ($K_D$) refers to the dissociation rate constant ($k_d$, time$^{-1}$) divided by the association rate constant ($k_a$, time$^{-1}$ M$^{-1}$). Equilibrium dissociation constants can be measured using any known method in the art. The antibodies of the present invention are high affinity antibodies. Such antibodies have an affinity better than 500 nM, and often better than 50 nM or 10 nM. Thus, in some embodiments, the antibodies of the invention have an affinity in the range of 500 nM to 100 pM, or in the range of 50 or 25 nM to 100 pM, or in the range of 50 or 25 nM to 50 pM, or in the range of 50 nM or 25 nM to 1 pM.

As used herein, "cancer therapeutic agent" refers to an agent that when administered to a patient suffering from cancer, in a therapeutically effective dose, will cure, or at least partially arrest the symptoms of the disease and complications associated with the disease.

The terms "identical" or percent "identity," in the context of two or more polypeptide (or nucleic acid) sequences, refer to two or more sequences or subsequences that are the same or have a specified percentage of amino acid residues (or nucleotides) that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." "Substantially identical" sequences also includes sequences that have deletions and/or additions, as well as those that have substitutions, as well as naturally occurring, e.g., polymorphic or allelic variants, and man-made variants. As described below, the preferred algorithms can account for gaps and the like. Preferably, protein sequence identity exists over a region that is at least about 25 amino acids in length, or more preferably over a region that is 50-100 amino acids=in length, or over the length of a protein.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

An indication that two polypeptides are substantially identical is that the first polypeptide is immunologically cross reactive with the antibodies raised against the second polypeptide. Thus, a polypeptide is typically substantially identical to a second polypeptide, e.g., where the two peptides differ only by conservative substitutions.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" in some embodiments denotes that a protein gives rise to essentially one band in an electrophoretic gel. Preferably, it means that the protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "a" or "an" is generally intended to mean "one or more" unless otherwise indicated.

Introduction

The invention is based, in part, on the discovery that EphA3-expressing neoplastic blast and/or neoplastic stem cells in patients that have a myeloproliferative disorder can be killed by contacting the EphA3-expressing myeloproliferative disorder cells with an activating antibody and/or an antibody that induces ADCC. Accordingly, in one aspect, the invention provides methods of treating a CML, PV, ET, IM, AML, MDS, CMML, or JMML patient, comprising administering an activating anti-EphA3 antibody to the patient. In some embodiments, the methods of the invention comprise administering an anti-EphA3 antibody that induces ADCC to a CML, PV, ET, IM, AML, MDS, CMML, or JMML patient. In some embodiments, an anti-EphA3 antibody that is administered to a CML, PV, ET, IM, AML, MDS, CMML, or JMML patient (i) is an activating anti-EphA3 antibody and (ii) induces ADCC.

In some embodiments, an anti-EphA3 antibody for use in this invention does not block binding of EphA3 to ephrin, e.g., ephrin-A5. In some embodiments, the antibody dimerizes EphA3. In some embodiments, the antibody cross-links EphA3. In some embodiments, the antibody competes with Mab IIIA4 for binding to EphA3, e.g., such an antibody may bind to the same epitope as Mab IIIA4. In some embodiments, the antibody has an active isotype where the heavy chain constant domain can bind to Fc receptor present on immune effector cells, leading to ADCC.

Anti EphA3 Antibodies

The anti-EphA3 antibodies of the invention can be raised against EphA3 proteins, or fragments, or produced recombinantly. Any number of techniques can be used to determine antibody binding specificity. See, e.g., Harlow & Lane, Antibodies, A Laboratory Manual (1988) for a description of immunoassay formats and conditions that can be used to determine specific immunoreactivity of an antibody In some embodiments, the anti-EphA3 antibody is a polyclonal antibody. Methods of preparing polyclonal antibodies are known to the skilled artisan (e.g., Harlow & Lane, Antibodies, A Laboratory manual (1988); Methods in Immunology). Polyclonal antibodies can be raised in a mammal by one or more injections of an immunizing agent and, if desired, an adjuvant. The immunizing agent includes a EphA3 receptor protein, or fragment thereof.

In some embodiments, the anti-EphA3 antibody is a monoclonal antibody. Monoclonal antibodies may be prepared using hybridoma methods, such as those described by Kohler & Milstein, *Nature* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

Human monoclonal antibodies can be produced using various techniques known in the art, including phage display libraries (Hoogenboom & Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., *J. Immunol.* 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); Lonberg & Huszar, *Intern. Rev. Immunol.* 13:65-93 (1995).

In some embodiments the anti-EphA3 antibodies are chimeric or humanized monoclonal antibodies. As noted supra, humanized forms of antibodies are chimeric immunoglobulins in which a CDR of a human antibody is replaced by a CDR of a non-human species such as mouse, rat or rabbit having the desired specificity, affinity and capacity.

An antibody that is employed in the invention can be in numerous formats. In some embodiments, the antibody can include an Fc region, e.g., a human Fc region. For example, such antibodies include IgG antibodies that bind EphA3 and that have an active isotype. In some embodiments, the antibody can be an active fragment (e.g., it can dimerize EphA3) or can comprise a derivative of an antibody such as an Fab, Fab', F(ab')$_2$, Fv, scFv, or a single domain antibody ("dAb"). For example, in some embodiments, the antibody may be a F(ab')$_2$. Other exemplary embodiments of antibodies that can be employed in the invention include activating nanobodies or activating camellid antibodies. Such antibodies may additionally be recombinantly engineered by methods well known to persons of skill in the art. As noted above, such antibodies can be produced using known techniques. As appreciated by one of skill in the art, in some embodiments when an antibody is in a format that can be monovalent, e.g., an Fv or Fab format, the antibody may be employed as a multivalent antibody, such as a trivalent or tetravalent antibody. Methods of generating multivalent antibodies are known (see, e.g., King et al., *Cancer Res.* 54:6176-6185, 1994).

In many embodiments, an antibody for use in the invention has an Fc constant region that has an effector function, e.g., binds to an Fc receptor present on immune effector cells. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g., B cell receptor), and the like. Such effector functions generally require the Fc region to be combined with a binding domain (e.g. an antibody variable domain) and can be assessed using known assays (see, e.g., the references cited hereinbelow.)

Anti-EphA3 antibodies that have an active isotype and are bound to Fc-receptors on effector cells, such as macrophages, monocytes, neutrophils and NK cells, can induce cell death by ADCC.

The Fc region can be from a naturally occurring IgG1, or other active isotypes, including IgG3, IgM, IgA, and IgE. "Active isotypes" include antibodies where the Fc region comprises modifications to increase binding to the Fc receptor or otherwise improve the potency of the antibody. Such an Fc constant region may comprise modifications, such as mutations, changes to the level of glycosylation and the like, that increase binding to the Fc receptor. There are many methods of modifying Fc regions that are known in the art. For example, U.S. Patent Application Publication No. 20060039904 describes variants of Fc receptors that have enhanced effector function, including modified binding affinity to one or more Fc ligands (e.g., FcγR, C1q). Additionally, such Fc variants have altered antibody-dependent cell-mediated cytotoxicity (ADCC) and/or complement dependent cytotoxicity (CDC) activity. Other Fc variants include those disclosed by Ghetie et al., *Nat Biotech.* 15:637-40, 1997; Duncan et al, *Nature* 332:563-564, 1988; Lund et al., *J. Immunol* 147:2657-2662, 1991; Lund et al, *Mol Immunol* 29:53-59, 1992; Alegre et al, *Transplantation* 57:1537-1543, 1994; Hutchins et al., *Proc Natl. Acad Sci USA* 92:11980-

11984, 1995; Jefferis et al, *Immunol Lett.* 44:111-117, 1995; Lund et al., *FASEB J* 9:115-119, 1995; Jefferis et al, *Immunol Lett* 54:101-104, 1996; Lund et al, *J Immunol* 157:4963-4969, 1996; Armour et al., *Eur Jlmmunol* 29:2613-2624, 1999; Idusogie et al, *J Immunol* 164:4178-4184, 200; Reddy et al, *J Immunol* 164:1925-1933, 2000; Xu et al., *Cell Immunol* 200:16-26, 2000; Idusogie et al, *J Immunol* 166:2571-2575, 2001; Shields et al., *J Biol Chem* 276:6591-6604, 2001; Jefferis et al, *Immunol Lett* 82:57-65. 2002; Presta et al., *Biochem Soc Trans* 30:487-490, 2002; Lazar et al., *Proc. Natl. Acad. Sci. USA* 103:4005-4010, 2006; U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; 7,335,742; and 7,317,091; and PCT Publications WO 94/2935; WO 99/58572; WO 00/42072; WO 02/060919, and WO 04/029207, In some embodiments, the glycosylation of Fc regions may be modified. for example, a modification may be aglycosylation, for example, by altering one or more sites of glycosylation within the antibody sequence. Such an approach is described in further detail in U.S. Pat. Nos. 5,714,350 and 6,350,861. An Fc region can also be made that has an altered type of glycosylation, such as a hypofucosylated Fc variant having reduced amounts of fucosyl residues or an Fc variant having increased bisecting GlcNAc structures. Such carbohydrate modifications can be accomplished by, for example, expressing the antibody in a host cell with altered glycosylation machinery. Cells with altered glycosylation machinery, including yeast and plants, have been described in the art and can be used as host cells in which to express recombinant antibodies of the invention to thereby produce an antibody with altered glycosylation. Techniques for modifying glycosylation include those disclosed e.g., in Umana et al, *Nat. Biotechnol* 17:176-180, 1999; Davies, et al., *Biotechnol. Bioeng.* 74:288-294, 2001; Shields et al, *J Biol Chem* 277: 26733-26740, 2002; Shinkawa et al., *J Biol Chem* 278:3466-3473, 2003; Niwa et al. *Clinc. Cancer Res.* 1-:6248-6255, 2004; Presta et al., *Biochem Soc Trans* 30:487-490, 2002; Kanda et al, *Glycobiology* 17:104-118, 2006; U.S. Pat. Nos. 6,602,684; 6,946,292; and 7,214,775; U.S. Patent Application Publication Nos. 20070248600; 20070178551; 20080060092; 20060253928; PCT publications WO 00/61739; WO 01/292246; WO 02/311140; and WO 02/30954; and Potillegent™ technology (Biowa, Inc. Princeton, N.J.); and GlycoMAb™. glycosylation engineering technology (GLYCART biotechnology AG, Zurich, Switzerland). In a hypofucosylated antibody preparation, typically at least 50 to 70% of the antibody molecule, often at least 80% of the molecules, or at least 90% of the molecules, lack fucose.

In some embodiments of the invention, the antibody is additionally engineered to reduce immunogenicity, e.g., so that the antibody is suitable for repeat administration. Methods for generating antibodies with reduced immunogenicity include humanization and humaneering procedures and modification techniques such as de-immunization, in which an antibody is further engineered, e.g., in one or more framework regions, to remove T cell epitopes.

In some embodiments, the antibody is a HUMANEERED™ antibody. A HUMANEERED™ antibody is an engineered human antibody having a binding specificity of a reference antibody, obtained by joining a DNA sequence encoding a binding specificity determinant (BSD) from the CDR3 region of the heavy chain of the reference antibody to human $V_H$ segment sequence and a light chain CDR3 BSD from the reference antibody to a human $V_L$ segment sequence. Methods for generating such antibodies are provided in US patent application publication no. 20050255552 and US patent application publication no. 20060134098.

An antibody can further be de-immunized to remove one or more predicted T-cell epitopes from the V-region of an antibody. Such procedures are described, for example, in WO 00/34317.

In some embodiments, the variable region is comprised of human V-gene sequences. For example, a variable region sequence can have at least 80% identity, or at least 85% or at least 90% identity, or higher, to human germ-line V-gene sequences.

An antibody used in the invention can include a human constant region. The constant region of the light chain may be a human kappa or lambda constant region. The heavy chain constant region is often a gamma chain constant region, for example, a gamma-1 or gamma-3 constant region.

In some embodiments, e.g., where the antibody is a fragment, the antibody can be conjugated to another molecule, e.g., to provide an extended half-life in vivo such as a polyethylene glycol (pegylation) or serum albumin. Examples of PEGylation of antibody fragments are provided in Knight et al., *Platelets* 15:409, 2004 (for abciximab); Pedley et al., *Br. J. Cancer* 70:1126, 1994 (for an anti-CEA antibody); and Chapman et al., *Nature Biotech.* 17:780, 1999.

Antibody Specificity

An antibody for use in the invention activates EphA3 and/or kills EphA3$^+$ cells by ADCC. An example of an antibody suitable for use with the present invention is an antibody that has the binding specificity of mAb IIIA4. The monoclonal antibody mAb IIIA4 binds to the native EphA3 globular ephrin-binding domain (Smith et al., *J. Biol. Chem.* 279: 9522-9531, 2004; and Vearing et al., *Cancer Res.* 65:6745-6754, 2005). High affinity mAb IIIA4 binding to the EphA3 surface has little effect on the overall affinity of ephrin-A5 interactions with EphA3.

In some embodiments, a monoclonal antibody that competes with mAb IIIA4 for binding to EphA3, or that binds the same epitope as mAb IIIA4, is used. Any of a number of competitive binding assays can be used to measure competition between two antibodies for binding to the same antigen. For example, a sandwich ELISA assay can be used for this purpose. In an exemplary assay, ELISA is carried out by using a capture antibody to coat the surface of a well. A subsaturating concentration of tagged-antigen is then added to the capture surface. This protein will be bound to the antibody through a specific antibody:antigen interaction. After washing, a second antibody that is linked to a detectable moiety is added to the ELISA. If this antibody binds to the same site on the antigen as the capture antibody, or interferes with binding to that site, it will be unable to bind to the target protein as that site will no longer be available for binding. If however this second antibody recognizes a different site on the antigen it will be able to bind. Binding can be detected by quantifying the amount of detectable label that is bound. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine specificity. The ability of a particular antibody to recognize the same epitope as another antibody is typically determined by such competition assays.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

In some embodiments, the antibody binds to the same epitope as mAb IIIA4. The epitope for IIIA4 and human engineered derivatives resides in the N-terminal globular ligand binding domain of EphA3 (amino acids 29-202 in the partial human EphA3 sequence below):

(SEQ ID NO: 1)

```
  1  MDCQLSILLL LSCSVLDSFG ELIPQPSNEV NLLDSKTIQG ELGWISYPSH GWEEISGVDE

61  HYTPIRTYQV CNVMDHSQNN WLRTNWVPRN SAQKIYVELK FTLRDCNSIP LVLGTCKETF

121  NLYYMESDDD HGVKFREHQF TKIDTIAADE SFTQMDLGDR ILKLNTEIRE VGPVNKKGFY

181  LAFQDVGACV ALVSVRVYFK KC.
```

The IIIA4 antibody binds adjacent to but does not interfere substantially with binding of EphrinA5 to the receptor. The epitope for antibody IIIA4 has been further characterized by Smith et al., *J. Biol. Chem.* 279: 9522, 2004 using site-directed mutagenesis. In this analysis, mutation of Glycine at position 132 to Glutamic acid (G132E) abolishes binding to IIIA4. Mutation of Valine 133 to Glutamic acid (V133E) reduces binding of EphA3 to IIIA4 antibody approximately 100-fold. It has subsequently been observed by the inventors that Arginine 136 is also part of the epitope. This residue is changed to Leucine in the sequence of the highly conserved EphA3 protein in the rat (R136L). Rat EphA3 does not bind IIIA4 or a human engineered derivative of IIIA4. Thus, G132, V133 and R136 (bolded and underlined in the sequence above) are important amino acids within the IIIA4 epitope.

Binding Affinity

In some embodiments, the antibodies suitable for use with the present invention have a high affinity binding for human EphA3. For the purposes of this invention, high affinity binding between an antibody and an antigen exists if the dissociation constant ($K_D$) of the antibody is <about 10 nM, for example, about 5 nM, or about 2 nM, or about 1 nM, or less.

using CM5 sensor chips, as described by Krinner et al., (2007) *Mol. Immunol.* February; 44(5):916-25. (Epub 2006 May 11)).

The anti-EphA3 antibody can bind to any region of EphA3. In some embodiments, the anti-EphA3 antibody activates EphA3. Often, the antibody dimerizes EphA3. In some embodiments, the antibody clusters EphA3. In some embodiments, an anti-EphA3 antibody can also be employed that has an active isotype, such as an IgG1, IgG3, IgM, IgA, or IgE, and is cytotoxic to myeloproliferative disorder cells via ADCC. Antibodies for use in the invention can also be multivalent including forms of monomers that are cross-linked or otherwise multimerized to form multivalent antibodies.

In some embodiments, an antibody employed in the invention does not compete with an EphA3 ligand for binding to EphA3, whereas in other embodiments an EphA3 antibody for use in the invention can compete for binding of an EphA3 ligand such as an ephrin, e.g., ephrin-A5, to EphA3. Antibodies that compete with a ligand for binding to EphA3, can be identified using techniques as described above, where an ephrin ligand such as ephrin-A5, is used instead of another antibody for a competition analysis.

In exemplary embodiments, the anti-EphA3 antibody comprises the $V_L$ and $V_H$ regions of mAb IIIA4. In other embodiments, the anti-EphA3 antibody comprises CDRs 1, 2 and 3 of mAb IIIA4. In some embodiments, the anti-EphA3 antibody comprises CDR3 of mAb IIIA4. Table 1 provides CDR sequences (defined according to Kabat numbering) of antibodies that bind to the same epitope as mAb IIIA4. Affinity for EphA3 antigen was determined by ELISA. An antibody of the invention may thus also have heavy chain and/or lights chain CDRs set forth in Table 1.

TABLE 1

| antibody | CDRH1 (SEQ ID NO:) | CDRH2 (SEQ ID NO:) | CDRH3 (SEQ ID NO:) | AFFINITY (nM) |
|---|---|---|---|---|
| IIIA4 | SYWIN (2) | DIYPGSGNTNYDEKFKR (3) | SGYYEDFDS (4) | 2.5 |
| FA3AM-H12A | TYWIS (5) | DIYPGSGNTNYDEKFQG (6) | SGYYEEFDS (7) | 3.2 |
| K3D | TYWIS (5) | DIYPGSGNTNYDEKFEG (8) | SGYYEEFDS (7) | 25 |

| antibody | CDRL1 (SEQ ID NO:) | CDRL2 (SEQ ID NO:) | CDRL3 (SEQ ID NO:) | AFFINITY (nM) |
|---|---|---|---|---|
| IIIA4 | RASQEISGYLG (9) | AASTLDS (10) | VQYANYPYT (11) | 2.5 |
| FA3AM-H12A | RASQGIISYLA (12) | AASSLQS (13) | VQYANYPYT (11) | 3.2 |
| K3D | RASQGIISYLA (12) | AASSLQS (13) | VQYMNYPYT (14) | 25 |

A variety of methods can be used to determine the binding affinity of an antibody for its target antigen such as surface plasmon resonance assays, saturation assays, or immunoassays such as ELISA or RIA, as are well known to persons of skill in the art. An exemplary method for determining binding affinity is by surface plasmon resonance analysis on a BIAcore™ 2000 instrument (Biacore AB, Freiburg, Germany)

Antibodies as described herein for use in the invention can be identified using known assays for the characteristic of interest. Thus, antibodies can be identified by screening for the ability to activate EphA3 (e.g., using n apoptosis assay as described in the examples), the ability to induce ADCC (e.g., using an ADCC assay as described in the examples), and for binding specificity and affinity using assays described above.

Non Antibody EphA3 Binding Agents

Other proteins that bind to EphA3 and dimerize or activate EphA3 receptor may also be administered to a patient that has a leukemia or CMPD. Such proteins include a soluble Ephrin A5-Fc protein.

Other EphA3 binding agents include scaffolded proteins that bind EphA3. Thus, the EphA3 binding agent can be an "antibody mimetic" that targets and binds to the antigen in a manner similar to antibodies. When an antibody mimetic is used, the form of the mimetic is such that it dimerizes EphA3. For example, the antibody mimetic may be used in a dimeric or multivalent format.

Certain antibody mimetics use non-immunoglobulin protein scaffolds as alternative protein frameworks for the variable regions of antibodies. For example, Ku et al. (*Proc. Natl. Acad. Sci. U.S.A.* 92:6552-6556, 1995) discloses an alternative to antibodies based on cytochrome b562 in which two of the loops of cytochrome b562 were randomized and selected for binding against bovine serum albumin. The individual mutants were found to bind selectively with BSA similarly with anti-BSA antibodies.

U.S. Pat. Nos. 6,818,418 and 7,115,396 disclose an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling may be employed in vitro that is similar to the process of affinity maturation of antibodies in vivo.

Beste et al. (*Proc. Natl. Acad. Sci. U.S.A.* 96:1898-1903, 1999) disclose an antibody mimic based on a lipocalin scaffold (Anticalin®). Lipocalins are composed of a β-barrel with four hypervariable loops at the terminus of the protein. The loops were subjected to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies. Thus, Anticalins® are small, single chain peptides, typically between 160 and 180 residues, which provides several advantages over antibodies, including decreased cost of production, increased stability in storage and decreased immunological reaction.

U.S. Pat. No. 5,770,380 discloses a synthetic antibody mimetic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (*Cell Mol Biol* 49:209-216, 2003) describe a methodology for reducing antibodies into smaller peptidomimetics, they term "antibody like binding peptidomimetics" (ABiP) which may also be useful as an alternative to antibodies.

WO 00/60070 discloses a polypeptide chain having CTL4A-like β-sandwich architecture. The peptide scaffold has from 6 to 9 β-strands, wherein two or more of the polypeptide β-loops constitute binding domains for other molecules, such as antigen binding fragments. The basic design of the scaffold is of human origin, thus reducing the risk of inducing an immune response. The β-sandwich scaffold may have improved stability and pharmacokinetic properties in vivo when compared to standard antibodies as the molecule contains a second, non-immunoglobulin disulphide bridge. As antigen binding domains can be located at opposite ends of a single peptide chain, the β-sandwich also facilitates design of bispecific monomeric molecules.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics). Accordingly, non-antibody EphA3 binding agents can also include such compounds.

In some embodiments, the EphA3 binding agents employed in the invention competed with mAb IIIA4 for binding to EphA3. Such agents can be identified using known assays, such as the exemplary competition assays described herein.

Identification of Patients Who are Candidate for Treatment with Anti-Epha3

The invention also provides methods of determining whether a patient having a myeloproliferative disorder is a candidate for treatment with an anti-EphA3 antibody. The methods comprise detecting the expression of EphA3 on myeloproliferative disorder cells from the patient. In some embodiments, expression of EphA3 is detected on blast cells. In some embodiments, EphA3 expression is detected on stem cells. In some embodiments, EphA3 expression is detected on both blast and stem cells.

In some embodiments, a blood sample, e.g., a serum or plasma sample, from a myeloproliferative disorder patient can be evaluated for elevated levels (e.g., in comparison to a normal patient that does not have a myeloproliferative disorder) of soluble EphA3 to determine if the patient is a candidate for treatment with an anti-EphA3 antibody. In some embodiments, levels of soluble EphA3 can be determined in a patient to monitor the efficacy of treatment with an anti-EphA3 antibody. Soluble EphA3 can be detected using known immunoassays, e.g., an ELISA.

EphA3 expression can be detected using methods well known in the art. Often, an immunological assay can be used to detect levels of EphA3 protein. Immunological assays include ELISA, fluorescent-activated cell sorting, and the like. Alternatively EphA3 expression can be detected by detecting the level of mRNA encoding EphA3. Often, a nucleic acid amplification method, e.g., an RT-PCR is employed to quantify the amount of RNA.

A sample comprising myeloproliferative disorder cells is obtained from the patient for evaluating EphA3 expression.

The sample is often a peripheral blood sample, but other suitable samples, e.g., a bone marrow sample, may also be analyzed.

A patient is considered to be a candidate for treatment with an anti-EphA3 antibody if blast cells, stem cells, or both that are present in the sample comprising myeloproliferative disorder cells express EphA3. Accordingly, "an EphA3+ patient" as used here is a patient that shows EphA3 expression on myeloproliferative disorder cells relative to cells from normal controls, e.g., patients who do not have a hematopoietic disorder.

Treatment of Myeloproliferative Disorders

In one aspect, the methods of the present invention comprise administering an anti-EphA3 agent, typically an anti-EphA3 antibody, to a patient that has AML, CML, PV, ET, IM, MDS, CMML, or JMML and has neoplastic myeloproliferative disorder cells that express EphA3 on the cell surface. In some embodiments, an anti-EphA3 agent, such as an antibody, is administered to a patient that neoplastic myeloid stem cells (characterized as $CD34^+$, $CD123^+$ and $CD38^-$) that express EphA3 A patient, such as an AML patient, that is treated with the anti-EphA3 agent, e.g., an anti-EphA3, in accordance with the invention may therefore have both hematopoietic stem cells and blast cells that express EphA3. Other patients that are treated using methods and compositions described herein may express EphA3 only on blast cells. Still other patients may express EphA3 only on stem cells. In some embodiments, a patient treated with the anti-EphA3 antibody is an AML or MDS patient having myeloproliferative disorder blast cells that expresses EphA3 on the surface.

Leukemic and myeloproliferative disorder stem cells can be identified by commonly used techniques such as immunophenotyping using flow cytometry, or by in vitro cell culture techniques or in vivo transplantation experiments.

Stem cells are multipotent progenitor cells that may be further defined functionally as cells with self-renewing capacity (see, e.g., Reya et al., *Nature* 414:105-111, 2001, and references cited therein). This may be demonstrated, for example, in long-term culture initiating cell (LTC-IC) assays in which cells are cultured on irradiated bone-marrow stromal feeder cells. In this assay, the presence of stem cells is revealed by the ability to serially transfer colonies for extended periods (e.g., at least 5 weeks e.g. Guan and Hogge (2000) Leukemia 14: 2135). Serial transfer assays may also be carried out by culturing stem cell-derived colonies in methyl cellulose in the presence of growth factors, such as a combination of stem cell factor (SCF), interleukin-3 (IL3), granulocyte macrophage colony stimulating factor (GM-CSF) and erythropoietin (EPO).

In vivo transplantation to identify stem cells is carried out by passaging by serial transfer in mice with defective immune systems (SCID/NOD mice; van Rhenen et al., *Clin. Cancer. Res.* 11: 6520-6527, 2005).

In flow cytometry analysis, leukemic or chronic myeloproliferative disorder (CMPD) stem cells are typically present in the CD34-positive, CD38-negative cell compartment (although approximately 10% of AML cases are CD34-negative). Leukemic or CMPD stem cells can be identified in the CD38-negative cell compartment as CD123-positive cells (Jordan et al., *Leukemia* 14: 1777-1784, 2000) although other markers may also be used to identify stem cells including the presence of CD117, CD45RA or CD133.

Blast cells are unipotent cells that are able to participate in granulopoiesis. Blast cells are larger cells than normal human mononuclear and polymorphonuclear blood cells and can be identified by microscopy from blood smears or by flow cytometry analysis on the basis of high forward scatter (FSC) and side scatter (SSC) compared with monocytes and granulocytes.

The anti-EphA3 composition can be formulated for use in a variety of drug delivery systems. One or more physiologically acceptable excipients or carriers can also be included in the compositions for proper formulation. Suitable formulations for use in the present invention are found in *Remington: The Science and Practice of Pharmacy,* 21st Edition, Philadelphia, Pa. Lippincott Williams & Wilkins, 2005. For a brief review of methods for drug delivery, see, Langer, *Science* s249: 1527-1533 (1990).

The anti-EphA3 antibody for use in the methods of the invention is provided in a solution suitable for injection into the patient such as a sterile isotonic aqueous solution for injection. The anti-EphA3 antibody is dissolved or suspended at a suitable concentration in an acceptable carrier. In some embodiments the carrier is aqueous, e.g., water, saline, phosphate buffered saline, and the like. The compositions may contain auxiliary pharmaceutical substances as required to approximate physiological conditions, such as pH adjusting and buffering agents, tonicity adjusting agents, and the like.

The pharmaceutical compositions of the invention are administered to a patient that has a myeloproliferative disorder in an amount sufficient to at least partially arrest the disease or symptoms of the disease and its complications. An amount adequate to accomplish this is defined as a "therapeutically effective dose." A therapeutically effective dose is determined by monitoring a patient's response to therapy. Typical benchmarks indicative of a therapeutically effective dose are known in the art, depending on the disease. For example, therapeutic efficacy may be indicated by the decrease of the number of abnormal myeloid cells that are characteristic of the particular myeloid proliferation disorder in the blood or bone marrow.

The dose of the anti-EphA3 antibody is chosen in order to provide effective therapy for the patient and is in the range of about 0.1 mg/kg body weight to about 25 mg/kg body weight or in the range about 1 mg to about 2 g per patient. The dose is often in the range of about 0.5 mg/kg or about 1 mg/kg to about 10 mg/kg, or approximately about 50 mg to about 1000 mg/patient. In some embodiments, the antibody is administered in an amount less than about 0.1 mg/kg body weight, e.g., in an amount of about 20 mg/patient or less. The dose may be repeated at an appropriate frequency which may be in the range once per day to once every three months, depending on the pharmacokinetics of the antibody (e.g. half-life of the antibody in the circulation) and the pharmacodynamic response (e.g. the duration of the therapeutic effect of the antibody). In some embodiments where the antibody or modified antibody fragment has an in vivo half-life of between about 7 and about 25 days and antibody dosing is repeated between once per week and once every 3 months. In other embodiments, the antibody is administered approximately once per month.

Amounts that are administered that are effective will depend upon the severity of the disease and the general state of the patient's health, including other factors such as age, weight, gender, administration route, etc. Single or multiple administrations of the anti EphA3 antibody may be administered depending on the dosage and frequency as required and tolerated by the patient. In any event, the methods provide a sufficient quantity of the anti EphA3 antibody to effectively treat the myeloproliferative disorder.

An anti-EphA3 antibody or anti-EphA3 agonist binding agent, e.g., that induces dimerization or activates EphA3, can be used in combination with one or more additional therapeutic agents to treat the myeloproliferative disorder. Therapeutic agents that can be administered in conjunction with anti-EphA3 binding agents include compounds such as MYLOTARG® (gemtuzumab ozogamicin for injection); a tyrosine kinase inhibitor such as imatinib mesylate (GLEEVEC®), nilotinib (TASIGNA®), and dasatinib (SPRYCEL®); interferon-α, and various chemotherapeutic agents.

In some embodiments, an anti-EphA3 activating antibody an be used in combination with one or more additional therapeutic agents to treat a patient that has chronic myeloid leukemia where leukemic stem cells from the patient express EphA3. Such therapeutic agents include various chemotherapeutic agents and imatinib mesylate (GLEEVEC®).

In some embodiments, an anti-EphA3 antibody, e.g., an activating antibody, can be used in combination with one or more additional agents to treat acute myeloid leukemia. Such agents include cytosine arabinoside alone and in combination with daunorubicin.

In some embodiments, an anti-EphA3 activating antibody can be used in combination with one or more additional therapeutic agents to treat a patient that has a BCR-ABL negative CMPD. Such inhibitors include JAK2 inhibitors, which are known in the art and undergoing clinical evaluation.

Patients can receive one or more of these additional therapeutic agents as concomitant therapy. Alternatively, patients may be treated sequentially with additional therapeutic agents.

In some embodiments, an anti-EphA3 activating antibody is administered to a patient that has undergone a bone marrow transplant.

In some embodiments, an anti-EphA3 antibody, or other activating Epha3 binding agent, is administered by injection or infusion through any suitable route including but not limited to intravenous, subcutaneous, intramuscular, intranasal, or intraperitoneal routes. In some embodiments, the anti EphA3 antibody is diluted in a physiological saline solution for injection prior to administration to the patient. The antibody is administered, for example, by intravenous infusion over a period of between 15 minutes and 2 hours.

The following examples are provided by way of illustration only and not by way of limitation. Those of skill in the art will readily recognize a variety of non-critical parameters that could be changed or modified to yield essentially similar results.

EXAMPLES

Example 1

Identification of CMPDs and Leukemias that Express EphA3 on the Surface

Flow cytometry was used to evaluate the expression of EphA3 on the surface of tumor cells from patients diagnosed with a myeloproliferative disorder. Cells isolated from peripheral blood (buffy coat cell preparations; peripheral blood mononuclear cells (PBMC)) or bone marrow aspirates were suspended at $1 \times 10^6$ cells/0.1 ml in flow cytometry buffer (PBS, 2 mM EDTA, 2% fetal bovine serum, 0.05% sodium azide) with 1 μg normal IgG to block Fc-receptor binding (rat IgG; US Biological or anti-FcR antibodies). Anti-EphA3 antibody or negative control human IgG1 was added at 5 μg/ml and incubated on ice for 20 min. Cells were washed by dilution in flow cytometry buffer and centrifugation at 1000 rpm for 5 min. The cell pellet was resuspended in FITC-conjugated goat F(ab)'$_2$ anti-human IgG antibody (Caltag) diluted in flow cytometry buffer (1:20) and incubated on ice for 20 min. Cells were washed once by centrifugation and resuspended in flow cytometry buffer containing propidium iodide (Sigma) diluted 1:1000. Viable cells which exclude propidium iodide were analyzed by flow cytometry to identify EphA3-expressing cells in comparison with cells stained with negative control antibody.

Table 2 shows that EphA3 is detectable on the cell surface in a proportion of acute and chronic myeloid leukemias and in myeloproliferative disorders including idiopathic myelofibrosis and essential thrombocythemia peripheral blood mononuclear cells.

TABLE 2

Summary of Flow Cytometry screen of bone marrow and peripheral blood (PBMC) samples for surface EphA3 detected by flow cytometry

| Tumor type | Number of samples tested | EphA3 positive samples* | Samples positive for EphA3 (%) |
|---|---|---|---|
| AML | 41 | 26 | 63 |
| CML | 10 | 5 | 50 |
| MDS | 16 | 7 | 44 |
| IM (PBMC) | 1 | 1 | |
| ET (PBMC) | 1 | 1 | |
| PV (PBMC) | 2 | 1 | |

*Sample defined as positive if at least 5% of cells show higher immunofluorescence than the fluorescence intensity in samples stained with isotype control antibody Leukemic stem cells in AML were also evaluated for surface EphA3 expression. Bone marrow-derived cells from an AML patient were stained with antibodies to CD34, CD38 and CD123 to identify the leukemic stem cell population (characterized as CD34-positive, CD123-positive and CD38-negative). PE-conjugated anti-CD34; PEcy5-conjugated anti-CD38; and APC-conjugated anti-CD123 antibodies were used for flow cytometry analysis (50,000 events per sample). Binding of human engineered antibody specific for EphA3 to CD34, CD38-gated cells is shown in FIG. 1. All of the CD123-positive (CD34-positive and CD38-negative) leukemic stem cells were positive for EphA3 expression.

EphA3 was not detectable on normal hematopoietic CD34-positive stem cells (data not shown). Further, antibody to EphA3 did not interfere with normal hematopoiesis in in vitro colony formation assays.

Example 2

Evaluation of the Ability of an Anti-EphA3 Antibody to Induce Apoptosis of Myeloproliferative Disorder Cells This example demonstrates that an anti-EphA3 antibody induced apoptosis in myeloproliferative disorder cells.

Figure 4:
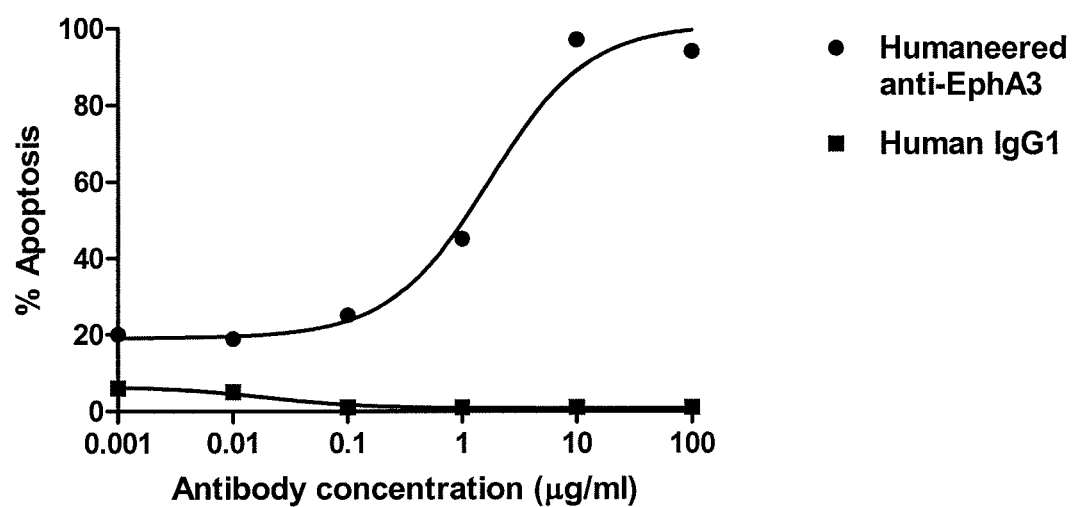
FIG. 4 provides data showing apoptosis activity of a human engineered antibody. Bone marrow cells (98% EphA3$^+$ by flow cytometry) from a CML patient were incubated in 96-well microtiter wells ($2\times10^5$ cells per well) with human engineered anti-EphA3 antibody or IgG1 control antibody at the concentrations shown for 24 hours. Cells were then stained with Annexin V-FITC and propidium iodide and analyzed by flow cytometry. Percent cells undergoing apoptosis (Annexin V-positive) are shown.

An engineered human activating antibody that binds to EphA3 was evaluated for the ability to induce apoptosis in vitro in primary cells isolated from patients or individuals suffering from myeloproliferative disorders. Cells were seeded at $2.5 \times 10^5$ cells/well in 96-well "U"-bottom plates in 0.1 ml culture medium (RPMI 1640 with 10% fetal bovine serum). Anti-EphA3 antibody or human IgG1 isotype control antibody was added to final concentrations between 10 µg/ml and 1 ng/ml and the plates were incubated at 37° C. and 5% carbon dioxide in a tissue-culture incubator for 24 hours. As a positive control for apoptosis induction, separate cell samples were incubated with camptothecin (10 µM; Calbiochem). At the end of the incubation, cells were harvested and washed by centrifugation at 1000 rpm for 5 min followed by incubation in 0.1 ml of 1× Annexin V binding buffer (BD Pharmingen, Cat #556547, component no. 51-66121E) containing 5 µl FITC-conjugated Annexin V (BD Pharmingen, component no. 51-65874x) and 5 µl Propidium Iodide (component no. 51-66211E) for 15 minutes at room temperature in the dark. Four hundred µl of 1× binding buffer was added to each tube and annexin V-staining apoptotic cells were identified by flow cytometry. FIG. 4 provides data showing apoptosis activity of a human engineered antibody.

The results shown in Table 3 demonstrate that the antibody induced apoptosis in several samples at levels comparable to camptothecin. In samples in which only a small proportion of the cells express EphA3, the anti-EphA3 antibody induced apoptosis in a similar small proportion of the cells, indicating that the induction of apoptosis is specific for EphA3-positive cells.

TABLE 3

Induction of apoptosis by an engineered human activating antibody that binds to EphA3.

| Sample | Disease | EphA3+ cells (%) | Anti-EphA3-mediated apoptosis (% cell death) | Camptothecin-mediated apoptosis (% cell death) |
|---|---|---|---|---|
| PB-1 | ET | 27 | 64 | 78 |
| PB-2 | PV | 6 | 1.8 | 73.2 |
| BM, 06 | AML | 65 | 85.5 | 59.8 |
| BM, 07 | AML | 80 | 46.7 | 47.8 |

(PB, peripheral blood; BM, bone marrow).

Example 3

Evaluation of the Ability of an Anti-EphA3 Antibody to Induce ADCC in Myeloproliferative Disorder Cells Preparation of Anti-EphA3 Antibody Deficient in α 1,6-fucose CHO cells expressing a recombinant engineered human anti-EphA3 antibody (IgG1k) were cultured in CHO-SFM II medium (Invitrogen) containing 2 µg/ml kifunensine to generate antibody with a modified glycosylation pattern defective in α 1,6-fucose as described (Zhou et al., *Biotechnol. Bioeng.* 99:652-665, 2008). Antibody purified by Protein A affinity chromatography showed significant reduction in the level of α 1,6-fucose determined by binding of *Lens culinaris* Lectin (Sigma) on protein blots with less than 10% antibody molecules containing this sugar moiety.

ADCC Assay

Human PBMC effector cells were isolated from buffy coat samples by Ficoll-hypaque density separation according to standard techniques. Primary mononuclear cells from bone marrow or peripheral blood from patients with leukemia or myeloproliferative disorders were used as target cells in ADCC assays. Tumor target cells were incubated for 16 hours with human effector cells at an effector:target ratio of 100:1 or 200:1 for PBMC. Lactate dehydrogenase (LDH) released from dead cells was determined by CytoTox 96 assay (Promega). In this assay, incubation of target cells with antibody in the absence of effector cells showed no detectable cytotoxicity.

Figure 2:
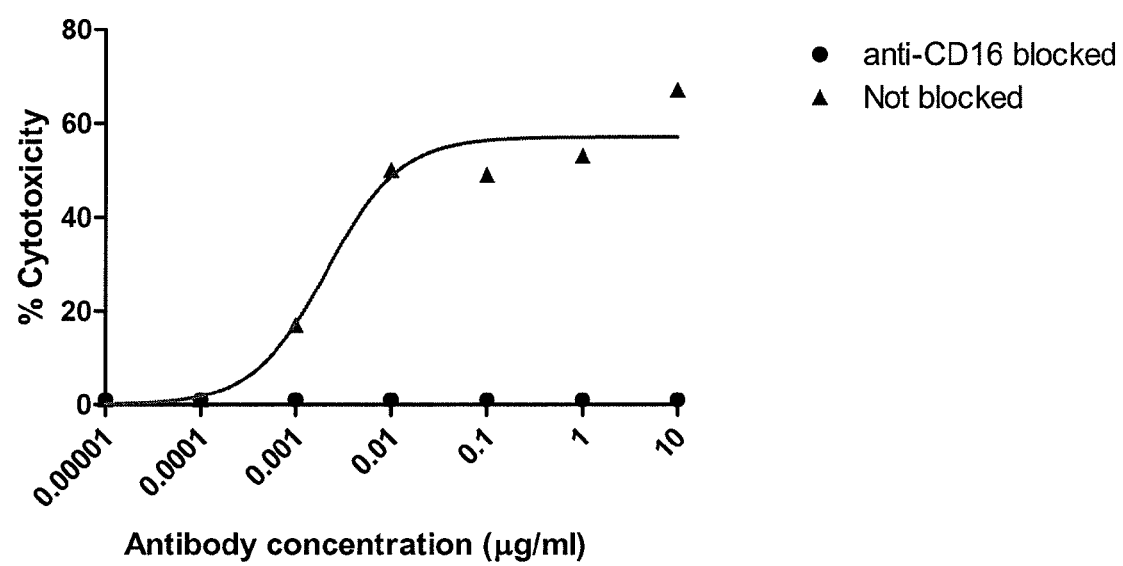
FIG. 2 provides data showing induction of CD16-mediated ADCC activity by an engineered human anti-EphA3 antibody. Peripheral blood mononuclear cells from a patient suffering from Essential Thrombocythemia were used as the target. PBMC effector cells from a normal individual were added at an effector:target ratio of 200:1 in the presence of anti-EphA3 antibody at the concentrations shown. ADCC activity was analyzed in the presence of anti-CD16 antibody to inhibit Fc-mediated effector function (circles) or in the absence of CD16-blocking antibody (triangles) by measuring LDH release after 16 hours.

Results of a representative ADCC assay in which killing of human essential thrombocythemia cells was induced by an anti-EphA3 antibody (IgG1k) in the presence of PBMC effector cells are shown in FIG. 2. The antibody showed potent ADCC activity in this assay. Inclusion of an antibody to CD16 abrogates the cytotoxic activity of the anti-EphA3 antibody, indicating that ADCC is mediated by the CD16 receptor (FcRIII). Anti-CD16 antibody (BD Pharmingen) was added at a concentration of 5 µg/ml.

Figure 3:
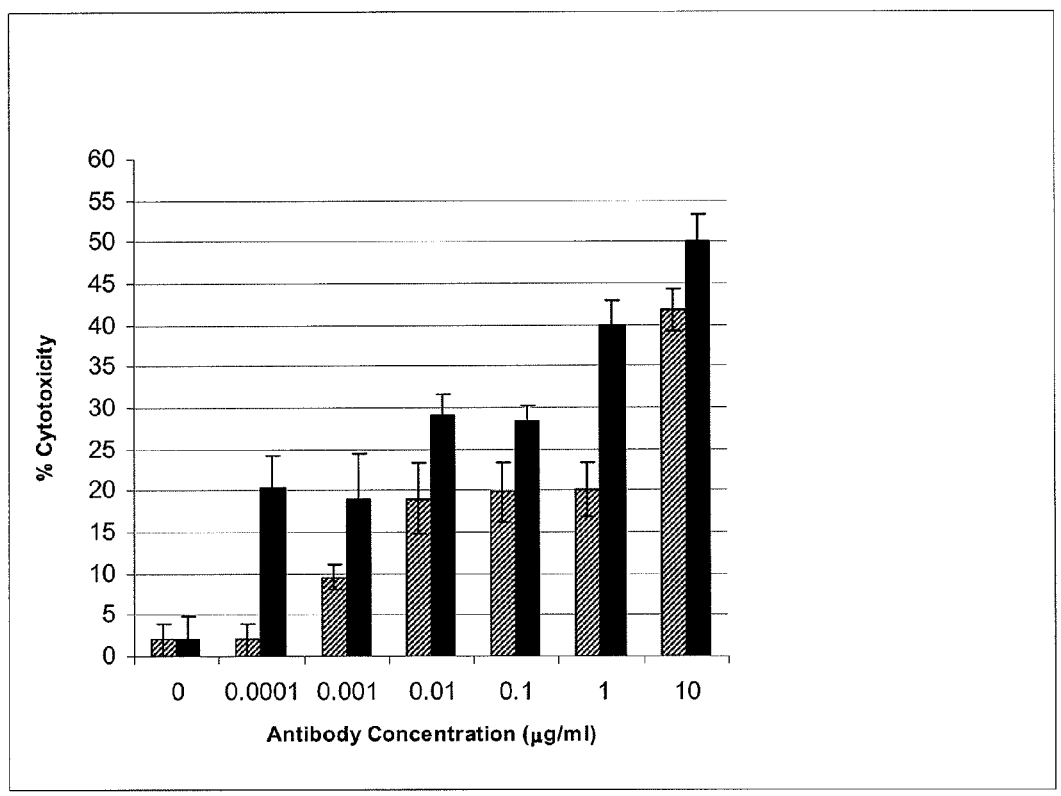
FIG. 3 provides data showing enhanced ADCC activity shown by an engineered human anti-EphA3 antibody (IgG1k) deficient in $\alpha$ 1,6 fucose. LK63 target cells were incubated with fucosylated anti-EphA3 antibody (hatched bars) or antibody deficient in $\alpha$1,6 fucose produced from kifunensine-treated cells (solid bars) at the concentrations shown. PBMC effector cells were added at an effector:target ratio of 100:1 for 16 hours and ADCC activity was determined by measuring LDH release.

The antibody preparation deficient in α 1,6 fucose was evaluated in comparison with fucosylated antibody in ADCC assays. In the assay shown in FIG. 3, a pre-B cell leukemia derived cell line LK63 was used as the target. The antibody deficient in α 1,6 fucose was significantly more potent than the fucosylated antibody in this assay. ADCC activity was detected with low levels of defucosylated antibody (0.1 ng/ml), a concentration at which fucosylated antibody showed no detectable ADCC activity.

The engineered human anti-EphA3 antibody also shows potent ADCC activity against primary human tumor cells from bone marrow samples from AML patients and shows ADCC activity against EphA3-positive cells in the peripheral blood of polycythemia vera patients as shown in Table 4.

TABLE 4

ADCC activity of an engineered human anti-EphA3 antibody against cells from patients with leukemia or myeloproliferative disease.

| Sample | Disease | EphA3+ cells (%) | Anti-EphA3-mediated ADCC (% cytotoxicity at 16 h) |
|---|---|---|---|
| PB-1 | ET | 27 | 70 |
| PB-2 | PV | 6 | 8 |
| BM, 06 | AML | 65 | 85.5 |
| BM, 07 | AML | 80 | 46.7 |
| BM, 157260 | AML | 65 | 70 |

(PB, peripheral blood; BM, bone marrow).

Table 5 summarizes data on the cell phenotype of EphA3-expressing cells from a larger panel of primary samples from bone marrow aspirates from AML and myelodysplastic syndrome patients and shows the proportion of cells in each sample killed by anti-EphA3 antibody either by direct induction of apoptosis or by effector-cell mediated ADCC activity. In these samples, in each case in which $CD123^+CD34^+CD38^-$ leukemic stem cells (LSC) could be identified, 100% of these LSC were also positive for EphA3 expression. In the majority of samples, there is good correlation between the percent of cells killed either by ADCC or apoptosis mediated by an engineered human anti-EphA3 antibody and the proportion of cells detected as positive for EphA3 by flow cytometry, indicating specificity of the antibody for EphA3-expressing cells.

TABLE 5

Summary of expression of EphA3 on malignant blast and leukemic stem cells: A human engineered antibody kills EphA3+ cells by two independent mechanisms.

| | Flow Cytometry Analysis on Bone Marrow Samples | | | | | Anti-EphA3 activity | |
|---|---|---|---|---|---|---|---|
| | | CD34+ Bone marrow | | Leukemic Stem Cells (CD34+CD38−CD123+) | | % Total | % Total Cells |
| Patient Sample | EphA3+ (% of total cells) | CD34+ (% of total cells) | EphA3+ (% of CD34+ cells) | LSC (% of total cells) | EphA3+ (% of LSC) | Cells Killed by ADCC | Killed by Apoptosis |
| AML1 | 0 | 0 | 0 | 0 | N/A | 0 | 0 |
| AML2 | 51 | 59 | 98 | 0 | N/A | 86 | 86 |
| AML3 | 83 | 81 | 100 | N/D | N/A | 47 | 50 |
| AML4 | 88 | 40 | 100 | 25 | 100 | 95 | 79 |
| AML5 | 55 | 90 | 64 | 0 | N/A | 72 | 79 |
| AML6 | 21 | 20 | 100 | 12 | 99 | 20 | 22 |
| AML7 | 16 | 77 | 12 | 10 | 100 | 20 | 15 |
| AML8 | 24 | 0 | 0 | 0 | N/A | 22 | 20 |
| AML9 | 31 | 16 | 36 | 0 | N/A | 40 | 45 |
| AML10 | 41 | 43 | 92 | 0 | N/A | 50 | 48 |
| AML11 | 55 | 56 | 99 | 0 | N/A | 65 | 75 |
| AML12 | 14 | 27 | 22 | 0 | N/A | 20 | 15 |
| MDS 1 | 15 | 17 | 22 | 1 | 100 | 25 | 20 |
| MDS 2 | 9 | 28 | 35 | 3 | 100 | 20 | 19 |

All publications, patent applications, accession numbers, and other references cited in this specification are herein incorporated by reference as if each individual publication or patent application were specifically and individually indicated to be incorporated by reference.

What is claimed is:

1. A method of killing myeloproliferative disorder cells that express EphA3 on the cell surface, the method comprising contacting the cells with an anti-EphA3 antibody, wherein the anti-EphA3 antibody (i) activates EphA3 and (ii) induces antibody-dependent cell-mediated cytotoxicity (ADCC).

2. A method of treating a patient that has a myeloproliferative disorder and has myeloproliferative disorder cells that express EphA3 on the cell surface, the method comprising administering a therapeutically effective amount of an anti-EphA3 antibody to the patient, wherein the anti-EphA3 antibody (i) activates EphA3 and (ii) induces ADCC.

3. The method of claim 1, wherein the myeloproliferative disorder cells are chronic myeloproliferative disorder (CMPD) cells.

4. The method of claim 3, wherein the CMPD cells are BCR-ABL negative CMPD cells.

5. The method of claim 3, wherein the CMPD cells are CML cells.

6. The method of claim 1, wherein the anti-EphA3 antibody comprises a human heavy chain gamma-1 or gamma-3 constant region.

7. The method of claim 1, wherein the anti-EphA3 antibody is hypofucosylated.

8. The method of claim 1, wherein the anti-EphA3 antibody competes with an antibody that comprises a $V_H$ region CDR1 having a sequence SYWIN (SEQ ID NO:2), a $V_H$ region CDR2 having a sequence DIYPGSGNTNYDEKFKR (SEQ ID NO:3), a $V_H$ region CDR3 having a sequence SGYYEDFDS (SEQ ID N0:4), a $V_L$ region CDR1 having a sequence RASQEISGYLG (SEQ ID NO:9), a $V_L$ region CDR2 having a sequence AASTLDS (SEQ ID NO:10), and a $V_L$ region CDR3 having a sequence VQYANYPYT (SEQ ID NO:11) for binding to EphA3.

9. The method of claim 1, wherein the anti-EphA3 antibody is a recombinant or chimeric antibody.

10. The method of claim 1, wherein the anti-EphA3 antibody is a human antibody.

11. The method of claim 1, wherein the anti-EphA3 antibody is a monoclonal antibody.

12. The method of claim 1, wherein the anti-EphA3 antibody comprises a $V_H$ region CDR1 having a sequence SYWIN (SEQ ID NO:2), a $V_H$ region CDR2 having a sequence DIYPGSGNTNYDEKFKR (SEQ ID NO:3), a $V_H$ region CDR3 having a sequence SGYYEDFDS (SEQ ID NO:4), a $V_L$ region CDR1 having a sequence RASQEISGYLG (SEQ ID NO:9), a $V_L$ region CDR2 having a sequence AASTLDS (SEQ ID NO:10), and a $V_L$ region CDR3 having a sequence VQYANYPYT (SEQ ID NO:11).

13. A method of killing myeloproliferative disorder cells that express EphA3 on the surface, the method comprising contacting the cells with an anti-EphA3 antibody that activates EphA3 or induces ADCC, wherein the myeloproliferative disorder cells are acute myeloid leukemia (AML) cells or myelodysplastic syndrome (MDS) cells.

14. A method of treating a patient that has a myeloproliferative disorder and has myeloproliferative disorder cells that express EphA3 on the cell surface, the method comprising administering a therapeutically effective amount of an anti-EphA3 antibody to the patient, wherein the anti-EphA3 antibody activates EphA3 or induces ADCC, wherein the myeloproliferative disorder is AML or MDS.

15. The method of claim 13, wherein the myeloproliferative disorder cells are AML cells.

16. The method of claim 13, wherein the anti-EphA3 antibody activates EphA3.

17. The method of claim 13, wherein the anti-EphA antibody comprises a human heavy chain constant region.

18. The method of claim 13, wherein the anti-EphA3 antibody competes for EphA3 binding with an antibody that comprises a $V_H$ region CDR1 having a sequence SYWIN (SEQ ID NO:2), a $V_H$ region CDR2 having a sequence DIYPGSGNTNYDEKFKR (SEQ ID NO:3), a $V_H$ region CDR3 having a sequence SGYYEDFDS (SEQ ID NO:4), a $V_L$ region CDR1 having a sequence RASQEISGYLG (SEQ ID NO:9), a $V_L$ region CDR2 having a sequence AASTLDS (SEQ ID NO:10), and a $V_L$ region CDR3 having a sequence VQYANYPYT (SEQ ID NO:11).

19. The method of claim 13, wherein the anti-EphA3 antibody is a $(Fab')_2$.

20. The method of claim 13, wherein the anti-EphA3 antibody is a recombinant or chimeric antibody.

21. The method of claim 13, wherein the anti-EphA3 antibody is a human antibody.

22. The method of claim 13, wherein the anti-EphA3 antibody is a monoclonal antibody.

23. The method of claim 13, wherein the anti-EphA3 antibody is a multivalent antibody that comprises a Fab, a Fab', or an Fv.

24. The method of claim 13, wherein the anti-EphA3 antibody comprises a $V_H$ region CDR1 having a sequence SYWIN (SEQ ID NO:2), a $V_H$ region CDR2 having a sequence DIYPGSGNTNYDEKFKR (SEQ ID NO:3), a $V_H$ region CDR3 having a sequence SGYYEDFDS (SEQ ID NO:4), a $V_L$ region CDR1 having a sequence RASQEIS-GYLG (SEQ ID NO:9), a $V_L$ region CDR2 having a sequence AASTLDS (SEQ ID NO:10), and a $V_L$ region CDR3 having a sequence VQYANYPYT (SEQ ID NO:11).

25. The method of claim 13, wherein the anti-EphA3 antibody induces ADCC.

26. The method of claim 13, wherein the anti-EphA3 antibody blocks binding of ephrinA5 ligand to EphA3.

27. The method of claim 13, wherein the anti-EphA3 antibody is hypofucosylated.

28. The method of claim 25, wherein the anti-EphA3 antibody has a human gamma-1 or gamma-3 constant region.

29. The method of claim 25, wherein the anti-EphA3 antibody blocks binding of ephrinA5 ligand to EphA3.

30. The method of claim 13, wherein the anti-EphA3 antibody has a human heavy chain gamma-2 or gamma-4 constant region.

* * * * *

SEQUENCE LISTING

<160> NUMBER OF SEQ ID NOS: 14

<210> SEQ ID NO 1
<211> LENGTH: 202
<212> TYPE: PRT
<213> ORGANISM: Artificial Sequence
<220> FEATURE:
<223> OTHER INFORMATION: synthetic human Eph receptor A3 (EphA3, Eph
      receptor tyrosine kinase A3, human embryo kinase,
      hek, eph-like tyrosine kinase 1, etk1, tyro4)
      partial sequence

<400> SEQUENCE: 1

Met Asp Cys Gln Leu Ser Ile Leu Leu Leu Leu Ser Cys Ser Val Leu
1               5                   10                  15

Asp Ser Phe Gly Glu Leu Ile Pro Gln Pro Ser Asn Glu Val Asn Leu
            20                  25                  30

Leu Asp Ser Lys Thr Ile Gln Gly Glu Leu Gly Trp Ile Ser Tyr Pro
        35                  40                  45

Ser His Gly Trp Glu Glu Ile Ser Gly Val Asp Glu His Tyr Thr Pro
    50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
            100                 105                 110

Leu Gly Thr Cys Lys Glu Thr Phe Asn Leu Tyr Tyr Met Glu Ser Asp
        115                 120                 125

Asp Asp His Gly Val Lys Phe Arg Glu His Gln Phe Thr Lys Ile Asp
    130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
            165                 170                 175

Lys Gly Phe Tyr Leu Ala Phe Gln Asp Val Gly Ala Cys Val Ala Leu
        180                 185                 190

Val Ser Val Arg Val Tyr Phe Lys Lys Cys
        195                 200

<210> SEQ ID NO 2
<211> LENGTH: 5
<212> TYPE: PRT
<213> ORGANISM: Artificial Sequence
<220> FEATURE:
<223> OTHER INFORMATION: synthetic anti-EphA3 antibody IIIA4 CDRH1

<400> SEQUENCE: 2

Ser Tyr Trp Ile Asn
1               5

<210> SEQ ID NO 3
<211> LENGTH: 17
<212> TYPE: PRT
<213> ORGANISM: Artificial Sequence
<220> FEATURE:
<223> OTHER INFORMATION: synthetic anti-EphA3 antibody IIIA4 CDRH2

<400> SEQUENCE: 3

Asp Ile Tyr Pro Gly Ser Gly Asn Thr Asn Tyr Asp Glu Lys Phe Lys
1               5                   10                  15

Arg

<210> SEQ ID NO 4
<211> LENGTH: 9
<212> TYPE: PRT
<213> ORGANISM: Artificial Sequence
<220> FEATURE:
<223> OTHER INFORMATION: synthetic anti-EphA3 antibody IIIA4 CDRH3

<400> SEQUENCE: 4

Ser Gly Tyr Tyr Glu Asp Phe Asp Ser
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic anti-EphA3 antibody FA3AM-H12A and
      K3D CDRH1

<400> SEQUENCE: 5

Thr Tyr Trp Ile Ser
1               5

<210> SEQ ID NO 6
<211> LENGTH: 17
<212> TYPE: PRT
<213> ORGANISM: Artificial Sequence
<220> FEATURE:
<223> OTHER INFORMATION: synthetic anti-EphA3 antibody FA3AM-H12A CDRH2

<400> SEQUENCE: 6

Asp Ile Tyr Pro Gly Ser Gly Asn Thr Asn Tyr Asp Glu Lys Phe Gln
1               5                   10                  15

Gly

```
<210> SEQ ID NO 7
<211> LENGTH: 9
<212> TYPE: PRT
<213> ORGANISM: Artificial Sequence
<220> FEATURE:
<223> OTHER INFORMATION: synthetic anti-EphA3 antibody FA3AM-H12A and
      K3D CDRH3

<400> SEQUENCE: 7

Ser Gly Tyr Tyr Glu Glu Phe Asp Ser
 1               5

<210> SEQ ID NO 8
<211> LENGTH: 17
<212> TYPE: PRT
<213> ORGANISM: Artificial Sequence
<220> FEATURE:
<223> OTHER INFORMATION: synthetic anti-EphA3 antibody K3D CDRH1

<400> SEQUENCE: 8

Asp Ile Tyr Pro Gly Ser Gly Asn Thr Asn Tyr Asp Glu Lys Phe Glu
 1               5                  10                  15

Gly

<210> SEQ ID NO 9
<211> LENGTH: 11
<212> TYPE: PRT
<213> ORGANISM: Artificial Sequence
<220> FEATURE:
<223> OTHER INFORMATION: synthetic anti-EphA3 antibody IIIA4 CDRL1

<400> SEQUENCE: 9

Arg Ala Ser Gln Glu Ile Ser Gly Tyr Leu Gly
 1               5                  10

<210> SEQ ID NO 10
<211> LENGTH: 7
<212> TYPE: PRT
<213> ORGANISM: Artificial Sequence
<220> FEATURE:
<223> OTHER INFORMATION: synthetic anti-EphA3 antibody IIIA4 CDRL2

<400> SEQUENCE: 10

Ala Ala Ser Thr Leu Asp Ser
 1               5

<210> SEQ ID NO 11
<211> LENGTH: 9
<212> TYPE: PRT
<213> ORGANISM: Artificial Sequence
<220> FEATURE:
<223> OTHER INFORMATION: synthetic anti-EphA3 antibody IIIA4 CDRL3

<400> SEQUENCE: 11

Val Gln Tyr Ala Asn Tyr Pro Tyr Thr
 1               5

<210> SEQ ID NO 12
<211> LENGTH: 11
<212> TYPE: PRT
<213> ORGANISM: Artificial Sequence
<220> FEATURE:
<223> OTHER INFORMATION: synthetic anti-EphA3 antibody FA3AM-H12A CDRL1

<400> SEQUENCE: 12

Arg Ala Ser Gln Gly Ile Ile Ser Tyr Leu Ala
```

```
-continued
1               5               10

<210> SEQ ID NO 13
<211> LENGTH: 7
<212> TYPE: PRT
<213> ORGANISM: Artificial Sequence
<220> FEATURE:
<223> OTHER INFORMATION: synthetic anti-EphA3 antibody FA3AM-H12A CDRL2

<400> SEQUENCE: 13

Ala Ala Ser Ser Leu Gln Ser
 1               5

<210> SEQ ID NO 14
<211> LENGTH: 9
<212> TYPE: PRT
<213> ORGANISM: Artificial Sequence
<220> FEATURE:
<223> OTHER INFORMATION: synthetic anti-EphA3 antibody K3D CDRL3

<400> SEQUENCE: 14

Val Gln Tyr Met Asn Tyr Pro Tyr Thr
 1               5
```